United States Patent
Ben-Ari et al.

(10) Patent No.: US 9,415,028 B2
(45) Date of Patent: Aug. 16, 2016

(54) COMPOUNDS FOR THE TREATMENT OF AUTISM

(75) Inventors: Yehezkel Ben-Ari, Marseilles (FR); Eric Lemonnier, Bohars (FR)

(73) Assignees: INSERM (INSTITUT NATIONAL DE LA SANTE ET DE LA RECHERCHE MEDICALE), Paris (FR); UNIVERSITE D'AIX MARSEILLE, Marseille (FR); CHU DE BREST, Brest (FR)

( * ) Notice: Subject to any disclaimer, the term of this patent is extended or adjusted under 35 U.S.C. 154(b) by 0 days.

(21) Appl. No.: 13/522,372

(22) PCT Filed: Jan. 13, 2011

(86) PCT No.: PCT/EP2011/050394
§ 371 (c)(1),
(2), (4) Date: Oct. 9, 2012

(87) PCT Pub. No.: WO2011/086126
PCT Pub. Date: Jul. 21, 2011

(65) Prior Publication Data
US 2013/0022622 A1    Jan. 24, 2013

(30) Foreign Application Priority Data
Jan. 15, 2010   (EP) .................................... 10305047

(51) Int. Cl.
*A61K 39/395* (2006.01)
*A61K 31/196* (2006.01)
*G01N 33/50* (2006.01)

(52) U.S. Cl.
CPC .......... *A61K 31/196* (2013.01); *G01N 33/5058* (2013.01)

(58) Field of Classification Search
None
See application file for complete search history.

(56) References Cited

U.S. PATENT DOCUMENTS

| 8,008,283 | B2 | 8/2011 | Hochman et al. |
|---|---|---|---|
| 2006/0089350 | A1 | 4/2006 | Hochman et al. |
| 2007/0032410 | A1 | 2/2007 | Quay et al. |
| 2012/0004225 | A1* | 1/2012 | Wanaski et al. ............ 514/235.5 |

FOREIGN PATENT DOCUMENTS

| CN | 102341380 A | 2/2012 |
|---|---|---|
| WO | 2006110187 A2 | 10/2006 |
| WO | 2009068668 A1 | 6/2009 |
| WO | 2010085352 A2 | 7/2010 |

OTHER PUBLICATIONS

Bradstreet et al., Med. Hypothesis, 2007, 68:979-87.*
The ICD-10 Classification of Mental and Behavioural disorders: Diagnostic criteria for research, 1993, World Health Organization.
Balena et al., "Coincident pre- and postsynaptic activity downregulates NKCC1 to hyperpolarize ECl during development", European Journal of Neuroscience, 2008, vol. 27, pp. 2402-2412.
Ben-Ari et al., "GABA: a pioneer transmitter that excites immature neurons and generates primitive oscillations", Physiology Reviews, 2007, vol. 87, pp. 1215-1284.
Ben-Ari, Yehezkel, "Excitatory actions of gaba during development: the nature of the nurture", Nature Reviews Neuroscience, Sep. 2002, vol. 3, pp. 728-739.
Ben-Ari, Yehezkel, "Neuro-archaeology: pre-symptomatic architecture and signature of neurological disorders", Trends in Neuroscience, 2008, vol. 31, pp. 626-636.
Blatt et al., "GABAergic cerebellar system in autism: a neuropathological and developmental perspective", International Review of Neurobiology, 2005, vol. 71, pp. 167-178.
Cohen et al., "On the origin of interictal activity in human temporal lobe epilepsy in vitro", Science, 2002, vol. 298, pp. 1418-1421.
Delpire et al., "Human and murine phenotypes associated with defects in cation-chloride cotransport", Annual Review of Physiology, 2002, vol. 64, pp. 803-843.
Delpire et al., "Deafness and imbalance associated with inactivation of the secretory Na—K—2Cl co-transporter", Nature Genetics, 1999, vol. 22, pp. 192-195.
Delpire, E., "Cation-Chloride Cotransporters in Neuronal Communication", News in Physiological Sciences, 2000, vol. 15, pp. 309-312.
Dzhala et al., "NKCC1 transporter facilitates seizures in the developing brain", Nature Medicine, 2005, vol. 11, No. 11, pp. 1205-1213.
Fiumelli et al., "Role of activity-dependent regulation of neuronal chloride homeostasis in development", Current Opinion in Neurobiology, 2007, vol. 17, pp. 81-86.
Fiumelli et al., "Modulation of GABAergic transmission by activity via postsynaptic Ca2+-dependent regulation of KCC2 function", Neuron, 2005, vol. 48, pp. 773-786.
Gagnon et al., "Characterization of SPAK and OSR1, regulatory kinases of the Na—K—2Cl cotransporter", Molecular and Cellular Biology, 2006, vol. 26, No. 2, pp. 689-698.
Woodin et al., "Coincident pre- and postsynaptic activity modifies GABAergic synapses by postsynaptic changes in Cl-transporter activity", Neuron, 2003, vol. 39, pp. 807-820.
Guinchat et al., "Pre-, peri- and neonatal risk factors for autism", Acta Obstetricia et Gynecologica Scandinavica, 2012, vol. 91, pp. 287-300.
Hill et al., "Understanding autism: insights from mind and brain", Phil. Trans. R. Soc. Lond. B, 2003, vol. 358, pp. 281-289.
Hill et al., "Executive dysfunction in autism", Trends in Cognitive Sciences, 2004, vol. 8, No. 1, pp. 26-32.
Huberfeld et al., "Ictal brain hyperperfusion contralateral to seizure onset: the SPECT mirror image", Epilepsia, 2006, vol. 47, No. 1, pp. 123-133.

(Continued)

*Primary Examiner* — Olga N Chernyshev
(74) *Attorney, Agent, or Firm* — Young & Thompson

(57) ABSTRACT

A compound which inhibits the importation of chloride into neurons and a compound which improve the outflow of chloride from neurons for the use in treatment of autism, a pharmaceutical composition for use in the treatment of autism including such compound and a pharmaceutically acceptable carrier are described.

3 Claims, No Drawings

(56) References Cited

OTHER PUBLICATIONS

Huberfeld et al., Perturbed chloride homeostasis and GABAergic signaling in human temporal lobe epilepsy, Journal of Neurosciences, 2007, vol. 27, No. 37, pp. 9866-9873.

Hussman, John P., "Suppressed GABAergic inhibition as a common factor in suspected etiologies of autism", Journal of Autism and Developmental Disorders, 2001, vol. 31, No. 2, pp. 247-248.

Hultman et al., "Perinatal risk factors for infantile autism", Epidemiology, 2002, vol. 13, No. 4, pp. 417-423.

Kahle et al., "The bumetanide-sensitive Na—K—2Cl cotransporter NKCC1 as a potential target of a novel mechanism-based treatment strategy for neonatal seizures", Neurosurgical Focus, 2008, vol. 25, No. 3, pp. E22.

Kahle et al., "Roles of the cation-chloride cotransporters in neurological disease", Nature Clinical Practice Neurology, 2008, vol. 4, No. 9, pp. 490-503.

Khalilov et al., "In vitro formation of a secondary epileptogenic mirror focus by interhippocampal propagation of seizures", Nature Neuroscience, 2003, vol. 6, No. 10, pp. 1079-1085.

Khalilov et al., "Epileptogenic actions of GABA and fast oscillations in the developing hippocampus", Neuron, 2005, vol. 48, pp. 787-796.

Levy et al., "Novel treatments for autistic spectrum disorders", Mental retardation and developmental disabilities research reviews, 2005, vol. 11, pp. 131-142.

Li et al., "Patterns of cation-chloride cotransporter expression during embryonic rodent CNS development", European Journal of Neuroscience, 2002, vol. 16, pp. 2358-2370.

Marshall et al., "Pharmacokinetics and pharmacodynamics of bumetanide in critically ill pediatric patients", Journal of Clinical Pharmacology, 1998, vol. 38, pp. 994-1002.

Nardou et al., "Bumetanide, an NKCC1 antagonist, does not prevent formation of epileptogenic focus but blocks epileptic focus seizures in immature rat hippocampus", Journal of Neurophysiology, 2009, vol. 101, pp. 2878-2888.

Oblak et al., "Decreased GABAA receptors and benzodiazepine binding sites in the anterior cingulate cortex in autism", Autism Research, 2009, vol. 2, No. 4, pp. 205-219.

O'Donnell et al., "The role of the blood-brain barrier Na—K—2Cl cotransporter in stroke", Advances in Experimental Medicine and Biology, 2004, vol. 559, pp. 67-75.

Payne et al., "Cation-chloride co-transporters in neuronal communication, development and trauma", Trends in Neurosciences, 2003, vol. 26, pp. 199-206.

Persico et al., "Searching for ways out of the autism maze: genetic, epigenetic and environmental clues", Trends in Neuroscience, 2006, vol. 29, No. 7, pp. 349-358.

Pobbe et al., "Oxytocin receptor knockout mice display deficits in the expression of autism-related behaviors", Hormones and Behavior, 2012, vol. 61, pp. 436-444.

Rivera et al., "The K+/Cl-co-transporter KCC2 renders GABA hyperpolarizing during neuronal maturation", Nature, 1999, vol. 397, pp. 251-255.

Van Kooten et al., "Autism: neuropathology, alterations of the GABAergic system, and animal models", International Review of Neurobiology, 2005, vol. 71, pp. 1-26.

Spitzer et al., "Action potentials, calcium transients and the control of differentiation of excitable cells", Current Opinion in Neurobiology, 1994, vol. 4, pp. 70-77.

Sullivan et al., "Pharmacokinetics of bumetanide in critically ill infants", Clinical Pharmacology & Therapeutics, 1996, vol. 60, pp. 405-413.

Witte et al., "Diuretic therapeutics in the pediatric patient", American Journal of Cardiology, 1986, vol. 57, pp. 44A-53A.

Bourgeron, Thomas, "A synaptic trek to autism", Current Opinion in Neurobiology, 2009, vol. 19, pp. 231-234.

Bourreau et al., "Validation of the repetitive and restricted behaviour scale in autism spectrum disorders", European Child and adolescent psychiatry, 2009, vol. 18, No. 11, pp. 675-682.

Di Lalla et al., "Domains of the Childhood Autism Rating Scale: relevance for diagnosis and treatment", Journal of Autism and Developmental Disorders, 1994, vol. 24, No. 2, pp. 115-128.

Kanner, Leo, "Autistic disturbances of affective contact", Nervous Child, 1943, vol. 2, pp. 217-250.

Patterson, Paul H., "Maternal infection: window on neuroimmune interactions in fetal brain development and mental illness", Current Opinion in Neurobiology, 2002, vol. 12, pp. 115-118.

Rheims et al., "Greater response to placebo in children than in adults: a systematic review and meta-analysis in drug-resistant partial epilepsy", PLoS Medicine, 2008, vol. 5, No. 8, e166, pp. 1223-1237.

Sandler, Adrian, "Placebo effects in developmental disabilities: implications for research and practice", Mental Retardation and Developmental Disabilities Research Reviews, 2005, vol. 11, pp. 164-170.

Schopler et al., "Toward objective classification of childhood autism: Childhood Autism Rating Scale (CARS)", Journal of Autism and Developmental disorders, 1980, vol. 10, No. 1, pp. 91-103.

International Search Report, dated Mar. 16, 2011, from corresponding PCT application No. PCT/EP2011/050394.

Erickson et al., "STX209 (Arbaclofen) for autism spectrum disorders: an 8-week open-label study," J Autism Dev Disord. Apr. 2014;44(4):958-64.

Velazquez et al., "Control by drugs of renal potassium handling," Annu. Rev. Pharmacol. Toxicol. 1986;26:293-309.

Nakamura et al., "Investigation of brain serotonergic dysfunction in high-functioning autism," Ann. Rep. Mitsubishi Pharma Res. Found. 2005 37: 191-197.

Li et al., "Propofol Facilitates Glutamatergic Transmission to Neurons of the Ventrolateral Preoptic Nucleus," Anesthesiology. Dec. 2009; 111(6): 1271-1278.

Belenky et al., "Cell-type distribution of chloride transporters in the rat suprachiasmatic nucleus," Neuroscience. Feb. 17, 2010; 165(4): 1519-37.

\* cited by examiner

COMPOUNDS FOR THE TREATMENT OF AUTISM

FIELD OF THE INVENTION

The invention relates to a compound which inhibits the importation of chloride into neurons or a compound which improve the outflow of chloride from neurons for use in the treatment of autism.

BACKGROUND OF THE INVENTION

Infantile Autistic Syndrome Disorders (ASD) include a wide range of abnormalities including a genuine incapacity to organise affective relations, behavioural anomalies in reciprocal social interactions, verbal and non verbal communication, limited interest in the surrounding environment associated with stereotyped movements and repetitive plays (Kanner, 1943; Levy and Hyman, 1993; Levy and Hyman, 2005; Adrien et al., 2001; Blanc et al., 2005; Bourreau et al., 2009). Research to date indicates that a genetic predisposition may play a role in the disease but one or more environmental factors must be in place for symptoms to occur including environmental contaminants and possibly maternal exposures during gestation (Persico and Bourgeron, 2006; Bourgeron, 2009; Patterson, 2002). It is suggested that genetic and environmental hazards will alter developmental programs leading to cortical and/or sub-cortical malformations and the formation of misplaced/ misconnected neuronal ensembles. The first symptoms occur before 3 years of age with most likely an earlier origin. There is at present no efficient biological/pharmaceutical treatment to ASD.

Brain maturation is associated with a developmental sequential expression of voltage gated, receptor synapse driven channels and brain patterns (Spitzer et al., 1994; Ben Ari et al., 2007). The developmental shifts of the actions of the inhibitory transmitter GABA is but one example of these changes. Immature neurons have a higher $(Cl^-)_i$ than adults leading to paradoxical excitatory actions of GABA (Ben Ari, 2002; Ben Ari et al., 2007). This is due to an early expression of the co-transporter NKCC1 that imports chloride and a late operation of KCC2 that export chloride form neurons (Kahle and Staley, 2008; Rivera et al., 1999; Dzhala et al., 2005; Delpire et al., 1999; Delpire, 2000; Li et al., 2002). In addition, the regulation of $(Cl^-)_i$ is dynamic and altered by even brief episodes of enhanced activity (Balena and Woodin, 2008; Fiumelli et al., 2005; Fiumelli and Woodin, 2007; Woodin et al., 2003) and more persistently by a variety of insults, lesions, seizures and neurological disorders (Khalilov et al., 2003; Khalilov et al., 2005; Cohen et al., 2002; Huberfeld et al., 2006; Huberfeld et al., 2007). Consequently, diuretic agents that reduce $(Cl^-)_i$ constitute novel antiepileptic and neuro-protective agents (Dzhala et al., 2005; Nardou et al., 2009; Kahle et al., 2008; Payne et al., 2003). In keeping with this, clinical tests are presently being conducted to that aim in infantile epilepsies.

Bumetanide (Bum) (Cohen, 1981; Feit, 1981) is a classical diuretic that selectively antagonises the co-transporter NKCC1—thereby reducing $(Cl^-)_i$ (Delpire et al., 1999; Delpire and Mount, 2002). Bum has been extensively utilised in adults since 1975 and in children since 1986 and its pharmacokinetic in adults and children and its side effects are well known (Lopez-Samblas et al., 1997; Sullivan et al., 1996; Witte et al., 1986; Marshall et al., 1998). Bum is used in acute (oedema following head trauma) and long term conditions including broncho-pulmonary dysplasia, nephritic syndromes or heart congestions (O'Donnell et al., 2004; Mackie et al., 1986; Sullivan et al., 1996) and has been recently reported to reduce seizure severity in a case report (Kahle et al., 2009). The use of Bum is safe provided that it is accompanied with continuous clinical and biological surveillance notably in children.

The inventors have now investigated in 5 autistic infants the effects of bum with ongoing clinical and biological surveillance. They were selected with no a priori from a large group of ASD children placed in institutions or at home to provide a variety of cases. The diuretic was administered (1 mg/24 h, 0.5 mg twice a day) and the treatment continued for 3 months, a minimal duration considered to be sufficient for an evaluation of the effects on IAS. We report a significant improvement of the IAS manifestations in the 5 children. These observations call for wide range screening of the use of Bum in IAS and more generally in autism.

SUMMARY OF THE INVENTION

The inventors have made the hypothesis that an antagonist of the NKCC co-transporter which inhibits the importation of chloride into neurons and thereby reduces intracellular concentrations may be useful for the treatment of autism.

Thus the invention relates to a compound which inhibits the importation of chloride into neurons and a compound which improve the outflow of chloride from neurons for use in the treatment of autism.

In another aspect, the invention relates to a pharmaceutical composition for use in the treatment of autism comprising a compound according to the invention and a pharmaceutically acceptable carrier.

DETAILED DESCRIPTION OF THE INVENTION

Definitions

Throughout the specification, several terms are employed and are defined in the following paragraphs.

As used herein, the term "autism" denotes a family of disorders of neural development that is characterized by impaired social interaction and communication, restricted and repetitive behaviour accompanied with other deficits. These signs all begin before a child is three years old. Autism affects information processing in the brain by altering how nerve cells and their synapses connect and organize; how this occurs is not well understood. The two other autism spectrum disorders (ASD) are Asperger syndrome, which lacks delays in cognitive development and language, atypical autism, diagnosed when full criteria for the other two disorders are not met, and PDD-NOS when pervasive developmental disorder are not specified.

As used herein, NKCC for "Na—K—Cl co-transporter" denotes a protein that assists in the active transport of sodium, potassium, and chloride into and out of cells. There are several varieties, or isoforms, of this membrane transport protein, notably NKCC1 and NKCC2. NKCC1 is widely distributed throughout the body but also in the brain and in particular in the developing animal and human brain. It acts to augment intracellular chloride in neurons and thereby to render GABA more excitatory. Extensive investigations indicate that blocking NKCC1 reduce intracellular chloride thereby augmenting the inhibitory actions of GABA. In vivo and in vitro studies have now indicated that genetic and/or pharmacological blockade of NKCC1 reduces early network activity.

As used herein, the term KCC for "potassium chloride co-transporter" denotes a co-transporter of chloride. There are several varieties, or isoforms, notably KCC2. KCC2 is found in many organs notably in the brain acts to remove intracellular chloride and thereby to augment the inhibitory actions of GABA. Blockers of KCC2 transform GABA to excitatory and facilitate the generation of seizures and genetic invalidation of KCC2 is lethal in mice. KCC2 is also expressed relatively late in development paralleling the shift of the actions of GABA from excitatory to inhibitory. Also, a wide range of insults and seizures remove functional KCC2 thereby leading to persistent excitatory actions of GABA and further seizures.

As used herein, the term "diuretic" denotes any drug that elevates the rate of urination and thus provides a means of forced diuresis. There are several categories of diuretics. All diuretics increase the excretion of water from bodies, although each class does so in a distinct way.

As used herein, the term "loop diuretics" denotes diuretics that act on the ascending loop of Henle in the kidney.

As used herein, the term "treating" or "treatment", denotes reversing, alleviating, inhibiting the progress of, or preventing the disorder or condition to which such term applies, or reversing, alleviating, inhibiting the progress of, or preventing one or more symptoms of the disorder or condition to which such term applies.

Antagonists and Uses Thereof

A first object of the invention relates to a compound which inhibits the importation of chloride into neurons or a compound which improve the outflow of chloride from neurons for use in the treatment of autism.

In a preferred embodiment, the compound according to the invention inhibits the NKCC co-transporter or activates the KCC co-transporter.

In another preferred embodiment, the compound according to the invention is an antagonist of NKCC co-transporter or an agonist of KCC co-transporter.

In one embodiment, said NKCC antagonist or KCC agonist may be a low molecular weight antagonist, e. g. a small organic molecule (natural or not).

The term "small organic molecule" refers to a molecule (natural or not) of a size comparable to those organic molecules generally used in pharmaceuticals. The term excludes biological macromolecules (e. g., proteins, nucleic acids, etc.). Preferred small organic molecules have a size range up to about 5000 Da, more preferably up to 2000 Da, and most preferably up to about 1000 Da.

In another embodiment, NKCC antagonist or KCC agonist of the invention may consist in an antibody which inhibits NKCC or activates KCC or an antibody fragment which inhibits NKCC or activates KCC.

Antibodies directed against NKCC or KCC can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against NKCC or KCC can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-NKCC or anti-KCC single chain antibodies. NKCC antagonists or KCC agonists useful in practicing the present invention also include anti-NKCC antibody fragments or anti-KCC antibody fragment including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to NKCC or KCC.

Humanized anti-NKCC antibodies or anti-KCC antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, NKCC antagonists or KCC agonists may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Small inhibitory RNAs (siRNAs) can also function as inhibitors of NKCC co-transporter gene expression for use in the present invention. NKCC co-transporter gene expression can be reduced by contacting a subject or cell with a small double stranded RNA (dsRNA), or a vector or construct causing the production of a small double stranded RNA, such that NKCC co-transporter gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of NKCC co-transporter gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of NKCC co-transporter mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of NKCC co-transporter gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing NKCC co-transporter. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

In preferred embodiment, the compound which inhibits the NKCC co-transporter is a diuretic.

In another preferred embodiment, the diuretic is a loop diuretic.

In a preferred embodiment, the compound according to the invention is a NKCC1 antagonist.

In another preferred embodiment, the compound according to the invention is bumetanide.

In a preferred embodiment, the compound according to the invention is selected from furosemide, ethacrynic acid, torsemide, azosemide, muzolimine, piretanide, tripamide and the like; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; and analogs and functional derivatives of such compounds.

In a preferred embodiment, an analog according to the invention may have a formula as described in the patent application WO2006110187.

In a preferred embodiment, the analog may be bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)n-i-ethyl ester, bumetanide benzyltrimethyl-ammonium salt, and bumetanide cetyltrimethylammonium salt.

In another preferred embodiment, the analog may be furosemide aldehyde, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethylammonium salt, furosemide cetyltrimethylammonium salt, furosemide N,N-dimethylglycolamide ester, furosemide methoxy(polyethyleneoxy)n-i-ethyl ester, furosemide pivaxetil ester and furosemide propaxetil ester.

In another preferred embodiment, the analog may be piretanide aldehyde, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzylltrimethylammonium salt, piretanide cetylltrimethylammonium salt, piretanide N,N-dimethylglycolamide ester, piretanide methoxy(polyethyleneoxy)n-i-ethyl ester, piretanide pivaxetil ester and/or piretanide propaxetil ester.

In another preferred embodiment, the analog may be tetrazolyl-substituted azosemides (such as methoxymethyl tetrazolyl-substituted azosemides, methylthiomethyl tetrazolyl-substituted azosemides and N-mPEG350-tetrazolyl-substituted azosemides), azosemide benzyltrimethylammonium salt and/or azosemide cetyltrimethylammonium salt.

In another preferred embodiment, the analog may be pyridine-substituted torsemide quaternary ammonium salts or the corresponding inner salts (zwitterions). Examples include, but are not limited to, methoxymethyl pyridinium torsemide salts, methylthiomethyl pyridinium torsemide salts and N-mPEG350-pyridinium torsemide salts.

In a preferred embodiment, the compound according to the invention is a KCC2 agonist.

In a preferred embodiment, the compound according to the invention is a compound which inhibits the level of the NKCC protein on the cell surface or improves the level of the KCC protein on the cell surface.

In another preferred embodiment, the cell is a neuron.

Another object of the invention relates to a method for treating autism comprising administering to a subject in need thereof with a compound which inhibits the importation of chloride into neurons or a compound which improve the outflow of chloride from neurons.

In one aspect, the invention relates to a method for treating autism comprising administering to a subject in need thereof a NKCC antagonist as above described.

Compounds of the invention may be administered in the form of a pharmaceutical composition, as defined below.

Preferably, said compound which inhibits the importation of chloride into neurons or which improve the outflow of chloride from neurons, preferably said antagonist of NKCC or said agonist of KCC, is administered in a therapeutically effective amount.

By a "therapeutically effective amount" is meant a sufficient amount of compound to treat and/or to prevent diseases as described previously.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Compounds according to the invention may be used for the preparation of a pharmaceutical composition for use in the treatment of autism.

Hence, the present invention also provides a pharmaceutical composition comprising an effective dose of a compound which inhibits the NKCC co-transporter, preferably a NKCC antagonist or which activates the KCC co-transporter, according to the invention.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Pharmaceutical composition according to the invention may also contain other compounds, which may be biologically active or inactive. For example, one or more treatment agents of the present invention may be combined with another agent, in a treatment combination, and administered according to a treatment regimen of the present invention. Such combinations may be administered as separate compositions, combined for delivery in a complementary delivery system, or formulated in a combined composition, such as a mixture or a fusion compound. Additionally, the aforementioned treatment combination may include a BBB permeability enhancer and/or a hyperosmotic agent.

Alternatively, compounds of the invention which inhibits the NKCC co-transporter or activates the KCC co-transporter can be further identified by screening methods as hereinafter described.

Screening Methods

Another object of the invention relates to a method for screening a compound which inhibits the NKCC co-transporter of activates the KCC co-transporter.

In particular, the invention provides a method for screening a NKCC antagonist or a KCC agonist for the treatment of autism.

For example, the screening method may measure the binding of a candidate compound to NKCC or KCC, or to cells or membranes bearing NKCC or KCC or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist).

Furthermore, screening methods may test whether the candidate compound results in a signal generated by an antagonist of NKCC or an agonist of KCC, using detection systems appropriate to cells bearing the receptor.

In a particular embodiment, the screening method of the invention comprises the step consisting of:

a) providing neurons expressing NKCC or KCC on their surface:

b) incubating said cells with a candidate compound;

c) determining whether said candidate compound binds to and inhibits NKCC or binds to and activates KCC; and d) selecting the candidate compound that binds to and inhibits NKCC or binds to and activates KCC.

In one embodiment, the NKCC co-transporter or the KCC co-transporter used in the screening method may be its orthologs and derivatives as defined in the present invention.

In general, such screening methods involve providing appropriate cells which express NKCC or KCC, its orthologs and derivatives thereof on their surface. In particular, a nucleic acid encoding NKCC or KCC may be employed to transfect cells to thereby express the receptor of the invention. Such a transfection may be accomplished by methods well known in the art.

In a particular embodiment, cells are selected from the group consisting of glial cells, neuronal cells, neurones, transfected cell lines for investigations or renal cells of any species (mouse, human . . . ).

The screening method of the invention may be employed for determining an antagonist or agonist by contacting such cells with compounds to be screened and determining whether such compound inhibits or activates the co-transporter.

The determination of the inhibition of NKCC can be assessed by determining the cell viability. A compound is deemed to decrease cell viability if it is negative in any one the methods described below as examples of cell rescue activity.

According to a one embodiment of the invention, the candidate compound of may be selected from a library of compounds previously synthesised, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. No. 5,475,096 and U.S. Pat. No. 5,270,163. Further illustratively, the candidate compound may be selected from the group of antibodies directed against NKCC or KCC.

Such the method may be used to screen NKCC antagonists or KCC agonists according to the invention.

The invention will be further illustrated by the following tables and examples. However, these examples and figures should not be interpreted in any way as limiting the scope of the present invention.

TABLE 1

Summary of patients included in the study.
4 girls and one boy aged between 3 years
and 8 months to 11 years and 5 months with
classical autistic signs (F84.0 de l'ICD 10).

| | age | sex | diagno | ADI1 | ADI2 | ADI3 | ADI4 |
|---|---|---|---|---|---|---|---|
| 1 | 8 yrs 11mths | M | F84.00 | 18 (10) | 13 (8) | 5 (3) | 5 (1) |
| 2 | 3 yrs 8 mths | F | F84.00 | 20 (10) | 8 (7) | 4 (3) | 5 (1) |
| 3 | 8 yrs 7 mths | M | F84.00 | 21 (10) | 8 (7) | 5 (3) | 4 (1) |
| 4 | 11 yrs 5 mths | M | F84.00 | 24 (10) | 14 (7) | 4 (3) | 5 (1) |
| 5 | 10 yrs 1 mths | M | F84.00 | 17 (10) | 20 (8) | 4 (3) | 3 (1) |

TABLE 2

Summary scores of the effects of bumetanide in the five patients (C = controls before the treatment, Bum = months after bumetanide).

| | 1 | | 2 | | 3 | | 4 | | 5 | |
|---|---|---|---|---|---|---|---|---|---|---|
| | C | Bum | C | Bum | C | Bum | C | Bum | C | Bum |
| Cars total | 38.5 | 28 | 40.5 | 36 | 38 | 30 | 53.5 | 49 | 32 | 28 |
| CARS nb item sup á 3 | 7 | 1 | 7 | 4 | 9 | 4 | 14 | 11 | 3 | 1 |
| ABC total | 84 | 57 | 79 | 49 | 89 | 62 | 93 | 79 | 46 | 36 |
| ABC1 | 20 | 17 | 9 | 3 | 20 | 12 | 15 | 15 | 18 | 17 |
| ABC2 | 9 | 1 | 19 | 11 | 12 | 5 | 26 | 19 | 10 | 7 |
| ABC3 | 12 | 6 | 10 | 6 | 13 | 3 | 15 | 12 | 3 | 1 |
| ABC4 | 39 | 28 | 41 | 29 | 32 | 33 | 37 | 33 | 15 | 11 |
| ABC5 | 4 | 5 | 0 | 0 | 12 | 9 | 0 | 0 | 0 | 0 |
| CGI1 | 5 | 5 | 7 | 7 | 5 | 5 | 7 | 7 | 4 | 4 |
| CGI2 | | 3 | | 3 | | 3 | | 3 | | 3 |
| CGI3 | | 3.00 | | 3.00 | | 2.00 | | 2.00 | | 3.00 |
| RDEG total | 49 | 28 | 60 | 48 | 39 | 37 | 75 | 69 | 49 | 40 |
| RDEG dysrégulation | 30 | 20 | 37 | 34 | 29 | 31 | 50 | 45 | 32 | 25 |
| RDEG lenteur | 12 | 5 | 14 | 8 | 6 | 5 | 15 | 14 | 10 | 9 |
| RRB total | 51 | 32 | 69 | 26 | 63 | 31 | 46 | 40 | 46 | 38 |
| RRB F1 | 21 | 15 | 21 | 13 | 12 | 6 | 16 | 14 | 11 | 9 |
| RRB F2 | 1 | 1 | 12 | 0 | 20 | 7 | 2 | 2 | 8 | 9 |
| RRB F3 | 17 | 6 | 18 | 9 | 19 | 9 | 18 | 16 | 5 | 5 |
| RRB F4 | 10 | 8 | 14 | 4 | 9 | 8 | 8 | 6 | 18 | 12 |

EXAMPLE

Material & Methods

The inventors have investigated in 5 autistic infants the effects of bum with ongoing clinical and biological surveillance. They were selected with no a priori from a large group of IAS children placed in institutions or at home to provide a variety of cases. The diuretic was administered (1 mg/24 h, 0.5 mg twice a day) and the treatment continued for 3 months, a minimal duration considered to be sufficient for an evaluation of the effects on IAS. We report a significant improvement of the IAS manifestations in the 5 children. These observations call for wide range screening of the use of Bum in IAS.

Children were diagnosed by experienced clinical psychiatrist using strict ICD-10 (OMS 1993) criteria for autistic disorder. These children had no history of neurological disease (normal EEG) Genetic tests systematically performed were negative indicating no identifiable mutation (Caryotype and fragile X). The ADI-R (Le Couteur et al., 1989; Lord et al., 1994) was collected for all participants to confirm the diagnoses. A clinical and biological examinations showed that none of the infants had a counter indication to bum (including blood ionogram, transaminases, alkaline phosphatases, uremia, creatinemia, creatinine clearance, γGT, glycemia notably). Since hypokalemia can induce wave burst arrhythmia, an ECG was performed to ensure that none of the patients had a lengthening of the QT because they have a higher propensity to generate arrhythmia. A clinical weekly surveillance was performed during the first, second and third month after treatment onset including blood sodium and potassium one week and 2 months after treatment onset. None of the infants had associated neurological disorders and none was under other treatment since at least three months.

To determine the possible therapeutic index efficacy, we relied on 5 classical behavioural determination of IAS severity including:

i) The Childhood Autism Rating Scale (CARS) is a 15-item rating scale that is used as a screening instrument and to assess the changes in symptoms of autism over time. These items comprise a broad range of symptoms of autism and are graded on a scale of 1 to 4, with 1 indicating normal behaviour and 4 denoting severely abnormal and/or inappropriate behaviour. The total score is determined by adding the 15 items. The number of items with a scale equal or superior to 3 is a strong indication of syndrome severity whereas a fall in either the total score after treatment and/or of the number of items equal or above 3, indicates improvement in the severity of autistic features (Rogers et al., 1993). This instrument was developed to aid the diagnostic process but is also sensitive to developmental changes in autistic symptoms (Schopler et al., 1980; Mesibov et al., 1989) and can be used to determine alterations produced by a treatment (Di Lalla and Rogers 1994 also see the French version of B. Rogé 1989). The notation was obtained during a session when the infants were placed in a game and animated discussion with the parents concerning the behaviour of the child during the last week.

ii) The ABC (Aberrant Behaviour Checklist) is a questionnaire filled by the treating doctor during a discussion with the parents (Aman et al., 1985; Rojahn and Helsel 1991). It is widely used in therapeutic trials to evaluate the impact of molecules on behaviour. ABC is a 58-item standardized problem with behaviour checklist that allows item rating on a 4-point scale from 0 (not occurring at all) to 3 (severe). The checklist questions comprise 5 subscales: Irritability (ABC1), Social Withdrawal (ABC2), Stereotypy (ABC3), Hyperactivity (ABC4) and Excessive Speech (ABCS). ABC has been validated on a large scale in the US and is adapted to studies of infantile populations. A French version has been used in the present study (Bouvard 2000).

iii) The Clinical Global Impressions (CGI) is widely used in the majority of clinical trials to examine disease severity. It is scaled from 0 to 7, with 1 being the normal value and it is considered a good estimation of the global situation of the patient. The clinician is asked to give a quotation of the disease as a function of his/her experience with other patients included in the investigation. The second impression provides an estimation of the global improvement of the patient and amelioration when compared to the onset of the trail. There are 7 levels; zero indicating no evolution. The third impression is the most useful as it concerns the therapeutic index and requires a single estimation that indicate both the therapeutic and side effects. This is utilised in research on novel generation psychotic agents with little side effects (Guy 1976).

iv) RDEG the regulation disorder Evaluation grid is a French scale of activity (96) that enables to detect the level of dys-regulation, and the slowness of response of the infants (Adrien 1996; Adrien et al. 2001, Blanc et al. 2005). The questionnaire is filled by the parents and concerns the behaviour of the children during the last week.

v) The Repetitive and Restricted Behaviour (RRB) scale (Bourreau et al 2009) is a 35-item standardized checklist, that allows item rating on a 5-point scale from 0—the behaviour is never expressed by the person—to 4—the behaviour is severely expressed and characteristic of the person). Factorial analysis produces four clinical meaningful factors, i.e. sensori-motor stereotypes (F 1), reaction to change (F2), restricted behaviours (F3) and modulation insufficiency (F4).

Results

A summary of the patients is shown in Table 1. 3 boys used a functional language, whereas the remaining boy and girl did not. The scores of ADI-R are above the threshold confirming the clinical diagnosis. Childs 1, 3, 5 follow a traditional school accompanied by an auxiliary person. During the year, child 1 and child 2 are followed by a psychologist using the ABA approach once a week for child 1 and 3 times a week for child 2). Child 2 has also 2 weekly session of orthophony relying on picture exchange communication system (PECS). Child 3 has an orthophonic treatment weekly and child 5 has no treatment. Child 4 is treated in a medical institution specialised in mentally retarded children. The test of bum was made during the summer vacation, when behavioural therapy and school were interrupted.

Table 2 shows the scores of the different scales used and those obtained before and after three months treatment. Before the treatment, 4 children (1, 2, 3, 4) had a CARS score above 36 indicating a severe IAS. Child 5 showed a medium degree of autism. Results show an improvement of the total scores of CARS, ABC, RDEG and RRB for all children three months after the treatment. CGI1 was not significantly altered but this test concerns the severity of the disease that at this stage does not reveal significant changes. We also observed a small global amelioration of CGI2 for the 5 children. Patients 1, 2 and 5 had an index of 3 in CGI3 indicating a moderate action with no side effects. Patients 3 and 4 had an index of 2 indicating a minimal action with no side effects. The number of items equal or above 3 with CARS was reduced by the treatment in the five children. The sub-score of ABC5, was not altered by the treatment. In the five children, ABC2, ABC3, ABC4, RDEG dysregulation, RDEG slowness, RRBF4; RRB F1 were ameliorated to a variable degree. In contrast, the results of ABC1, RRB F2, RRB F3 are heterogeneous.

Starting one week after the treatment and once monthly, a clinical surveillance was made including research of deshydratation, orthostatic hypotension, hyper-senstivity, cramps, asthenia, diarrheas, myalgia, arthralgia, nausea, dizziness. The levels of sodium and potassium remained stable (tests made a week and 2 months after the beginning of the treatment. No adverse effect was found.

Discussion

Present results suggest that bumetanide ameliorates behavioural aspects of IAS suggesting that the diuretic has a global action. To the best of our knowledge, this is the first report raising the possibility of chloride alterations in autism.

The conclusions derived form these observations are hampered by several limitations including the lack of randomized double blind and placebo investigations—due to the limited number of cases. Placebo effects are more prevalent in children than adults (Rheims et al., 2008) this also applies to autism (Sandler 2005). Clearly, wide scale investigations are needed to confirm or infirm the observations. We are aware of these limitations to demonstrate the positive effects of bumetanide and entangle its actions on IAS. Nevertheless, our observations indicate that bumetanide has no side effects with a general tolerance to the diuretic. Also, we were encouraged to present these observations by the dramatic behavioural amelioration suggested by the results and the insistence of the parents that their children are more present and their wish to pursue the treatment speaking in favour of a significant action of bum. In spite of the difficulty in translating this subjective notion, it is interesting to stress that the same term of presence was used by all parents.

It is not possible at present to determine whether bumetanide exerts a preferential action on one aspect of the symptomatology. The lack of effects of bumetanide on ABC5—inappropriate, excessive speech out of context—is expected because amelioration in 3 months of speech is unlikely to occur. In contrast almost all scores were ameliorated to variable degrees stressing the general action of bumetanide. Alteration of cognitive and emotional behaviour is a basic feature of IAS (Kanner, 1943; Hill and Frith, 2003; Hill, 2004; Bieberich and Morgan, 2004) and the fact that bumetanide enables a better cognitive regulation is perhaps to be correlated with the improved presence reported by the parents. The results of the subscales of ABC suggest an amelioration of states of vigilance and social interactions, stereotypic movements and hyperactivity again in keeping with the notion of cognitive regulation. The pharmaco-dynamic of bumetanide has been investigated in human neonates (Sullivan et al., 1996; Lopez-Samblas et al., 1997) and a recent report suggests that bumetanide reduces seizure severity in an epileptic child (Kahle et al., 2009). A wide range of experimental investigations suggest that bumetanide reduces seizure severity (Kahle and Staley, 2008; Kahle et al., 2008; Nardou et al., 2009). Bumetanide is currently being investigated as a novel treatment for neonatal seizures (EU FP7 Nemo project).

The observations are compatible with the working hypothesis that bumetanide enhances the efficacy of neuronal integrative processes by reducing intracellular chloride and reinforcing the inhibitory actions of GABA. The basic conceptual frame of these investigations is that neurons who fail to respect the developmental program keep immature features-including possibly high $(Cl-)I$ and other electrical and architectural properties (Ben-Ari, 2008). Other observations suggest a link between GABAergic signals and autism (Minshew, 1997; Hussman, 2001; Schmitz et al., 2005). Also, several brain imaging observations indicate a significant loss of GABA/benzodiazepines receptors in autism notably in the hippocampus, cerebellum and various limbic structures (Garreau et al., 1993; Oblak et al., 2009; Guptill et al., 2007; Blatt, 2005).

In conclusion, an emerging series of studies suggest that chloride accumulates during brain maturation in relation to various developmental malformations. Present observations suggest that a conventional diuretic that reduces this accumulation and acts to reinstate the inhibitory actions of GABA. may exert beneficial actions in autism calling for more detailed experimental and clinical studies on the links between GABA/$(Cl-)I$ and IAS.

REFERENCES

Throughout this application, various references describe the state of the art to which this invention pertains. The disclosures of these references are hereby incorporated by reference into the present disclosure.

Adrien J L, Rossignol-Deletang N, Martineau J, Couturier G, Barthelemy C (2001) Regulation of cognitive activity and early communication development in young autistic, mentally retarded, and young normal children. Dev Psychobiol 39:124-136.

Adrien J.-L (1996) Autisme du jeune enfant: développement psychologique et regulation de l'activité. Paris: Expansion scientifique Française.

Aman M G, Singh N N, Stewart A W et al. (1985) The Aberrant Behavior Checklist: a behaviour rating scale for assessment of treatment effects. American Journal of Mental Deficiency 89 (5): 485-491.

Balena T, Woodin M A (2008) Coincident pre- and postsynaptic activity downregulates NKCC1 to hyperpolarize E(Cl) during development. Eur J Neurosci 27:2402-2412.

Ben Ari Y (2002) Excitatory actions of GABA during development: The nature of the nurture. Nature Reviews Neuroscience 3:728-739.

Ben Ari Y, Gaiarsa J L, Tyzio R, Khazipov R (2007) GABA: A Pioneer Transmitter That Excites Immature Neurons and Generates Primitive Oscillations. Physiol Rev 87:1215-1284.

Ben-Ari Y (2008) Neuro-archaeology: pre-symptomatic architecture and signature of neurological disorders. Trends Neurosci 31:626-636.

Bieberich A A, Morgan S B (2004) Self-regulation and affective expression during play in children with autism or Down Syndrome: a short-term longitudinal study. J Autism Dev Disord 34:439-448.

Blanc R, Adrien J L, Roux S, Barthelemy C (2005) Dysregulation of pretend play and communication development in children with autism. Autism 9:229-245.

Blatt G J (2005) GABAergic cerebellar system in autism: a neuropathological and developmental perspective. Int Rev Neurobiol 71:167-178.

Bourgeron T (2009) A synaptic trek to autism. Curr Opin Neurobiol 19:231-234.

Bourreau Y., Roux S., Gomot M., Bonnet-Brilhault F., Barthélémy C. (2009) Validation of the repetitive and restricted behaviour scale in autism spectrum disorders. European Child and adolescent psychiatry, November 18(11): 675-682.

Bourreau Y, Roux S, Gomot M, Barthelemy C (2009) [Repetitive and restricted behaviours (RRB) in autism: clinical evaluation]. Encephale 35:340-346.

Bouvard M (2000) Liste des comportements aberrants-version traduite, Issy les moulineaux, EAP/ECPA.

Cohen I, Navarro V, Clemenceau S, Baulac M, Miles R (2002) On the origin of interictal activity in human temporal lobe epilepsy in vitro. Science 298:1418-1421.

Cohen M (1981) Pharmacology of bumetanide. J Clin Pharmacol 21:537-542.

Delpire E (2000) Cation-Chloride Cotransporters in Neuronal Communication. News Physiol Sci 15:309-312.

Delpire E, Lu J, England R, Dull C, Thorne T (1999) Deafness and imbalance associated with inactivation of the secretory Na—K—2Cl co-transporter. Nat Genet 22:192-195.

Delpire E, Mount D B (2002) Human and murine phenotypes associated with defects in cation-chloride cotransport. Annu Rev Physiol 64:803-843.

DiLalla D. L., Rogers S. J. (1994) Domains of the Childhood Autism Rating Scale: relevance for diagnosis and treatment. J. Autism Dev Disord. April 24(2):115-28

Dzhala V I, Talos D M, Sdrulla D A, Brumback A C, Mathews G C, Benke T A, Delpire E, Jensen F E, Staley K J (2005) NKCC1 transporter facilitates seizures in the developing brain. Nat Med 11:1205-1213.

Feit P W (1981) Bumetanide—the way to its chemical structure. J Clin Pharmacol 21:531-536.

Fiumelli H, Cancedda L, Poo M M (2005) Modulation of GABAergic transmission by activity via postsynaptic Ca2+-dependent regulation of KCC2 function. Neuron 48:773-786.

Fiumelli H, Woodin M A (2007) Role of activity-dependent regulation of neuronal chloride homeostasis in development. Current Opinion in Neurobiology 17:81-86.

Garreau B, Herry D, Zilbovicius M, Samson Y, Guerin P, Lelord G (1993) Theoretical aspects of the study of benzodiazepine receptors in infantile autism. Acta Paedopsychiatr 56:133-138.

Guptill J T, Booker A B, Gibbs T T, Kemper T L, Bauman M L, Blatt G J (2007) [3H]-flunitrazepam-labeled benzodiazepine binding sites in the hippocampal formation in autism: a multiple concentration autoradiographic study. J Autism Dev Disord 37:911-920.

Guy W. ECDEU (1976) Assessment Manual for psychopharmacology, National institute of Mental Health (Ed.). (Early Clinical Drug Evaluation Unit)

Hill E L (2004) Executive dysfunction in autism. Trends Cogn Sci 8:26-32.

Hill E. L., Frith U. (2003) Understanding autism: insights from mind and brain. Philos Trans R Soc Lond B Biol Sci. February 28; 358 (1430): 281-9.

Hussman J P. (2001) Suppressed gabaergic inhibition as a common factor in suspected etiologies of autism, J of Autism and Developmental Disorders. 31 (2): 247-248.

Huberfeld G, Wittner L, Clemenceau S, Baulac M, Kaila K, Miles R, Rivera C (2006) Perturbed Cl-homeostasis and gabaergic signaling in human temporal lobe epilepsy. Epilepsia 47:20.

Huberfeld G, Wittner L, Clemenceau S, Baulac M, Kaila K, Miles R, Rivera C (2007) Perturbed chloride homeostasis and GABAergic signaling in human temporal lobe epilepsy. J Neurosci 27:9866-9873.

Kahle K T, Barnett S M, Sassower K C, Staley K J (2009) Decreased seizure activity in a human neonate treated with bumetanide, an inhibitor of the Na(+)-K(+)-2Cl(−) cotransporter NKCC1. J Child Neurol 24:572-576.

Kahle K T, Staley K J (2008) The bumetanide-sensitive Na—K—2Cl cotransporter NKCC1 as a potential target of a novel mechanism-based treatment strategy for neonatal seizures. Neurosurg Focus 25:E22.

Kahle K T, Staley K J, Nahed B V, Gamba G, Hebert S C, Lifton R P, Mount D B (2008) Roles of the cation-chloride cotransporters in neurological disease. Nat Clin Pract Neurol 4:490-503.

Kanner L. (1943) Autistic disturbances of affective contact. Nervous Child 2: 217-50

Khalilov I, Holmes G L, Ben Ari Y (2003) In vitro formation of a secondary epileptogenic mirror focus by interhippocampal propagation of seizures. Nat Neurosci 6:1079-1085.

Khalilov I, Le Van Q M, Gozlan H, Ben Ari Y (2005) Epileptogenic Actions of GABA and Fast Oscillations in the Developing Hippocampus. Neuron 48:787-796.

Le Couteur A, Rutter M, Lord C, Rios P, Robertson S, Holdgrafer M, McLennan J (1989) Autism diagnostic interview: a standardized investigator-based instrument. J Autism Dev Disord 19:363-387.

Levy S E, Hyman S L (1993) Pediatric assessment of the child with developmental delay. Pediatr Clin North Am 40:465-477.

Levy S E, Hyman S L (2005) Novel treatments for autistic spectrum disorders. Ment Retard Dev Disabil Res Rev 11:131-142.

Li H, Tornberg J, Kaila K, Airaksinen M S, Rivera C (2002) Patterns of cation-chloride cotransporter expression during embryonic rodent CNS development. Eur J Neurosci 16:2358-2370.

Lopez-Samblas A M, Adams J A, Goldberg R N, Modi M W (1997) The pharmacokinetics of bumetanide in the newborn infant. Biol Neonate 72:265-272.

Lord C, Rutter M, Le Couteur A (1994) Autism Diagnostic Interview-Revised: a revised version of a diagnostic interview for caregivers of individuals with possible pervasive developmental disorders. J Autism Dev Disord 24:659-685.

Mackie K, DePasquale M, Cserr H F (1986) Increased permeability of a glial blood-brain barrier during acute hyper-osmotic stress. Am J Physiol 251:R1186-R1192.

Marshall J D, Wells T G, Letzig L, Kearns G L (1998) Pharmacokinetics and pharmacodynamics of bumetanide in critically ill pediatric patients. J Clin Pharmacol 38:994-1002.

Mesibov G B, Schopler E, Caison W (1989) The Adolescent and Adult Psychoeducational Profile: assessment of adolescents and adults with severe developmental handicaps. J Autism Dev Disord 19:33-40.

Minshew N I. (1997) In vivo brain chemistry of autism: 31P Magnetic resonance spectroscopy studies, in Bauman M L and Kemper T L, The neurobiology of autism, Baltimore: Johns Hopkins University Press.

Nardou R, Ben-Ari Y, Khalilov I (2009) Bumetanide, an NKCC1 antagonist, does not prevent formation of epileptogenic focus but blocks epileptic focus seizures in immature rat hippocampus. J Neurophysiol 101:2878-2888.

O'Donnell M E, Lam T I, Tran L, Anderson S E (2004) The role of the blood-brain barrier Na—K—2Cl cotransporter in stroke. Adv Exp Med Biol 559:67-75.

Oblak A, Gibbs T T, Blatt G J (2009) Decreased GABAA receptors and benzodiazepine binding sites in the anterior cingulate cortex in autism. Autism Res 2:205-219.

Patterson P H (2002) Maternal infection: window on neuroimmune interactions in fetal brain development and mental illness. Curr Opin Neurobiol 12:115-118.

Payne J A, Rivera C, Voipio J, Kaila K (2003) Cation-chloride co-transporters in neuronal communication, development and trauma. Trends Neurosci 26:199-206.

Persico A M, Bourgeron T (2006) Searching for ways out of the autism maze: genetic, epigenetic and environmental clues. Trends Neurosci 29:349-358.

Rheims S, Cucherat M, Arzimanoglou A, Ryvlin P (2008) Greater response to placebo in children than in adults: a systematic review and meta-analysis in drug-resistant partial epilepsy. PLoS Med 5:e166.

Rivera C, Voipio J, Payne J A, Ruusuvuori E, Lahtinen H, Lamsa K, Pirvola U, Saarma M, Kaila K (1999) The K+/Cl-co-transporter KCC2 renders GABA hyperpolarizing during neuronal maturation. Nature 397:251-255.

Rogé B. (1989) Echelle d'évaluation de l'autisme infantile-version traduite (CARS-T). Issy les moulineaux, EAP/ECPA.

Rogers S J, Ozonoff S, Maslin-Cole C (1993) Developmental aspects of attachment behavior in young children with pervasive developmental disorders. J Am Acad Child Adolesc Psychiatry 32:1274-1282.

Rojahn J, Helsel W J (1991) The Aberrant Behavior Checklist with children and adolescents with dual diagnosis. J Autism Dev Disord 21:17-28.

Sandler A. (2005) Placebo Effects in Developmental Disabilities: Implications for Research and Practice, Mental Retardation and Developmental Disabilities Research Reviews 11: 164-170.

Schmitz C, van K, I, Hof P R, van E H, Patterson P H, Steinbusch H W (2005) Autism: neuropathology, alterations of the GABAergic system, and animal models. Int Rev Neurobiol 71:1-26.

Schopler E, Reichler R J, De Vellis R F, Dally K. (1980) Toward Objective Classification of Childhood Autism: Childhood Autism Rating Scale (CARS), J. of Autism and Developmental disorders 10 (1): 91-103.

Spitzer N C, Gu X, Olson E (1994) Action potentials, calcium transients and the control of differentiation of excitable cells. Curr Opin Neurobiol 4:70-77.

Sullivan J E, Witte M K, Yamashita T S, Myers C M, Blumer J L (1996) Pharmacokinetics of bumetanide in critically ill infants. Clin Pharmacol Ther 60:405-413.

The ICD-10 Classification of Mental and Behavioural disorders: Diagnostic criteria for research (1993), World Health Organization.

Witte M K, Stork J E, Blumer J L (1986) Diuretic therapeutics in the pediatric patient. Am J Cardiol 57:44A-53A.

Woodin M A, Ganguly K, Poo M m (2003) Coincident Pre- and Postsynaptic Activity Modifies GABAergic Synapses by Postsynaptic Changes in Cl— Transporter Activity. Neuron 39:807-820.

The invention claimed is:

1. A method for treating autism in a subject in need thereof, comprising administering to the subject a therapeutically effective amount of a compound which is a Na—K—Cl co-transporter (NKCC) inhibitor and a loop diuretic, wherein said compound is bumetanide.

2. The method according to claim 1, wherein the compound is administered at a dosage level from 0.0002 mg/kg to about 20 mg/kg of body weight per day.

3. The method according to claim 1, wherein the subject in need thereof is a child showing signs of autism.

* * * * *